United States Patent [19]

Kedar et al.

[11] Patent Number: 4,772,469

[45] Date of Patent: Sep. 20, 1988

[54] PRODUCTION OF LYMPHOID TISSUE EFFECTOR CELLS REACTIVE AGAINST CANCER CELLS BY MEANS OF MER, AND USE THEREOF IN CANCER THERAPY

[76] Inventors: Eli Kedar, 2, Hagay Str., Beit Hakerem, Jerusalem; David W. Weiss, 20 Radak St., Rehavia, Jerusalem, both of Israel

[21] Appl. No.: 844,488

[22] Filed: Oct. 21, 1977

Related U.S. Application Data

[63] Continuation-in-part of Ser. No. 675,051, Apr. 8, 1976.

[30] Foreign Application Priority Data

Mar. 28, 1976 [IL] Israel .......................................... 49301

[51] Int. Cl.[4] ............................................. A61K 35/78
[52] U.S. Cl. ................................................... 424/195.1
[58] Field of Search ...................................... 424/195.1

[56] References Cited

PUBLICATIONS

Kedar et al., J. Natl. Cancer Inst. 60: 1097–1106 (1978).
Kedar, J. Immunol. Methods 26: 157–171 (1979).
Kedar et al., J. Immunol. Methods 28: 303–319 (1979).
Kedar et al., J. Immunol. Methods 16: 39–58.
Weiss, Proceedings of the 5th Berkeley Symposium, Berkeley, 1967, pp. 657–706.

*Primary Examiner*—Jerome D. Goldberg
*Attorney, Agent, or Firm*—Browdy and Neimark

[57] ABSTRACT

The addition of small amounts of MER to an in vitro culture of animal or human lymphocytes together with cancer cells will greatly potentiate the process by which the lymphocytes become actively cytotoxic to the specific type of cancer cells when injected in vivo. In some cases MER causes sensitization of the lymphocytes even when there is none without the MER. MER cultured in vitro with lymphocytes without specific cancer cells in the culture will cause non-specific cytotoxic sensitization of the lymphocytes. The sensitized cytotoxic reactive cells may be stored cryogenically for use in human cancer therapy.

5 Claims, No Drawings

PRODUCTION OF LYMPHOID TISSUE EFFECTOR CELLS REACTIVE AGAINST CANCER CELLS BY MEANS OF MER, AND USE THEREOF IN CANCER THERAPY

CROSS REFERENCE TO RELATED APPLICATIONS

The present application is a continuation-in-part of U.S. application Ser. No. 675,051 filed Apr. 8, 1976, the entire contents of which are hereby incorporated by reference.

FIELD OF THE INVENTION

The present invention concerns a method and means for combatting the development of neoplastic cells in the human body, i.e., for combatting the various human ailments generally referred to as cancer.

More particularly, the present invention relates to an improvement in the known method of stimulating animal and human lymphocytes to become actively cytotoxic to cancer cells by incubation in vitro in contact with the corresponding cancer cells.

BACKGROUND OF THE INVENTION

It has been known for several years that animal and human lymphocytes of one or several different types can be stimulated to become actively cytotoxic to cancer cells ("tumor cells") by incubation in vitro in contact with the corresponding cancer cells, even in circumstances where in vivo contact with the same neoplastic cells ("immunization" or "sensitization") fails to result in such activity. Bringing the lymphocytes and the cancer cells together in tissue culture in vitro for several days bestows specific killing capacity on the lymphocytes. This is sometimes referred to as "education" of the white blood cells.

In most cases normal, allogeneic (individual of same species, but differring genetically) lymphoid cell cultures have been employed but recently allogeneic, syngeneic (individual of the same species and of the same inbred strain) and autologous (cells of the same individual) tumor cells of both rodent and human origin have been utilized as stimulator cells. Kedar et al "In Vitro Induction of Cell-Mediated Immunity to Murine Leukemia Cells. I Optimization of Tissue Culture Conditions for the Generation of the Cytotoxic Lymphocytes", *Journal of Immunological Methods*, 13, (1976), 1-19, relates to such prior work and is hereby incorporated by reference as indicating the state of the art, particularly with respect to the required culture medium content and other culturing conditions to obtain optimum sensitization of the lymphocytes.

SUMMARY OF THE INVENTION

It has now been found in accordance with the present invention that the addition of small amounts of MER to the mixture potentiates dramatically this "education" process. Thus, in accordance with the present invention, large numbers of white blood cells may be extracted from a human donor, subjected to an education process against cancer and or leukemia cells, and the resulting product may be stored at low temperatures for use whenever required. The donor may be a leukemia patient in remission, a tumor patient at any time, or a healthy individual, and the preparation so obtained may be used for the treatment of the donor or of anybody else. The stimulated cells ("effector cells") appear to be cytotoxic specifically to the cancer cells against which they were sensitized. The sensitization is effective both for tumors of syngeneic and of allogeneic origin. In the syngeneic test systems, the effector cells have been shown not to be cytotoxically reactive against normal cells of the same syngeneic origin.

The term "MER" as used in the present specification and claims relates to a methanol-insoluble fraction of phenol-killed acetone-washed attenuated tubercle bacilli of the BCG (Bacillus Calmette Guerin) strain. MER is described in the literature and has been known for over twenty years. A description of its preparation is set forth on pages 2-4 of patent application Ser. No. 675,051 which has already been incorporated herein by reference.

In accordance with the present invention, not only lymphocytes but also macrophagic cells derived from mouse lymphoid tissues may become stimulated to anti-tumor cell cytotoxic reactivity following incubation in vitro with the tumor target cells in the presence of MER. For the purpose of the present specification and claims, all types of stimulated cytotoxic reactive cells will hereinafter be referred to as "lymphoid tissue effector cells" or as "effector cells".

It is extremely significant that in accordance with present invention, it has been discovered that the addition of MER to mouse lymphoid tissue cell-tumor target cell mixtures cell reactivity even in test systems where education does not occur in the absence of MER.

Further, in accordance with the present invention, MER may be added alone, without tumor cells, to a culture of lymphoid tissue cells in which case there will result the development of cytotoxic reactivity against a variety of tumor cells (nonspecific activation to cytotoxic capacity) on the part of at least some of the lymphoid tissue cells. This has also been observed and studied with white blood cells in the peripheral blood of human donors in which the non-specific cytotoxic activity against a variety of tumor cells includes even cells of xenogeneic origin (from another species).

The lymphoid tissue cells may be frozen to the temperature of liquid nitrogen and preserved at that temperature for long periods of time without destroying the viability of the cells or the capacity of such cells to be specifically and nonspecifically activated in vitro, or, if already sensitized or activated, to function as cytotoxic effector cells.

It is preferred that the MER be added to the mixed lymphoid cell-tumor cell culture within the initial 48 hours of culture and most preferably within the first 24 hours.

DETAILED DESCRIPTION OF PREFERRED EMBODIMENTS

As stated hereinabove, the techniques for the withdrawal of lymphocytes from the living body and their "education" towards reacting strongly against cancer cells has been reported in the literature and is known. One example of the improved effect obtainable with the aid of MER was demonstrated by the in vitro generation of cytotoxic effector cells from splenocytes derived from mice.

Experiment 1

$5 \times 10^6$ C57B1 or BALB/c splenocytes were incubated with $5 \times 10^4 - 5 \times 10^5$ mitomycin-C inactivated EL4 cells (of C57B1 origin) in a "one-way" mixed cell culture reaction. MER (the formulated suspension made available by the Division of Cancer Treatment, National Cancer Institute, Bethesda, Md., for clinical use) was added to the cultures in various amounts, from the beginning of incubation or on days +1 or +2. On day +6, the splenocytes were washed repeatedly with tissue culture medium, counted, and transferred in various amounts to culture tubes containing $2 \times 10^4$ chromium labeled EL4 cells. The cell mixtures were incubated for 3 hours, and the specific liberation of $^{51}Cr$ from the targets ascertained by the method described in Kedar et al, supra.

In a first series of trials, the in vitro influences of MER were tested on the generation of allogeneic BALB/c cytotoxic effector cells. The results of a representative experiment are presented in Table 1. It is seen that amounts of MER ranging from 66 to 0.8 μg elevated the cytotoxic capacity of the splenocytes for the target cells, whereas the largest amount tested, 200 μg, was frequently ineffective or inhibitory. None of these amounts of MER were toxic for the lymphoid cells.

TABLE 1

EFFECT OF MER IN VITRO ON SENSITIZATION OF BALB/c SPLENOCYTES TO C57Bl EL4 LEUKEMIA CELLS

| MER added (μg) to Cultures* at Beginning | Percent Specific $^{51}Cr$ Release from EL4 Cells in Contact with in vitro Sensitized Splenocytes at Effector/Target Cell ratios of | |
|---|---|---|
| | 30:1 | 10:1 |
| 0 (Control) | 64 | 29 |
| 200 | 69 | 39 |
| 66 | 94 | 63 |
| 22 | 100 | 56 |
| 7.3 | 80 | 44 |
| 2.4 | 75 | 44 |
| 0.8 | 83 | 47 |
| 0.3 | 52 | 27 |

*The total volume of each culture was 5 ml.

Each splenocyte preparation is a pool of cells derived from the spleens of 3-5 identically treated mice; each value represents the mean of triplicate determinations on each splenocyte pool. (This holds true as well for Tables 2-4).

Experiment 2

In a second protocol, the effects of MER were ascertained on syngeneic C57Bl splenocytes. Observations similar to those coming from the allogeneic system were made, as shown in Table 2. Quantities of MER from 22 μg downward to the smallest amount tested, 0.8 μg, had a potentiating effect, 66 μg exerted no discernible influence, and 200 μg was inhibitory. In further experiments, identical MER induced increments of cytotoxic acticity were found for syngeneic pooled lymph node cells as well.

TABLE 2

EFFECT OF MER IN VITRO IN SENSITIZATION OF C57Bl SPLENOCYTES TO C57Bl EL4 LEUKEMIA CELLS

| MER added (μg) to Cultures at Beginning | Percent Specific $^{51}Cr$ Release from EL4 Cells in Contact with in vitro Sensitized Splenocytes at Effector/Target Cell Ratios of | |
|---|---|---|
| | 100:1 | 30:1 |
| 0 (Control) | 20 | 15 |
| 200 | 12 | 6 |
| 66 | 19 | 14 |
| 22 | 40 | 38 |
| 7.3 | 60 | 39 |

TABLE 2-continued

EFFECT OF MER IN VITRO IN SENSITIZATION OF C57Bl SPLENOCYTES TO C57Bl EL4 LEUKEMIA CELLS

| MER added (μg) to Cultures at Beginning | Percent Specific $^{51}Cr$ Release from EL4 Cells in Contact with in vitro Sensitized Splenocytes at Effector/Target Cell Ratios of | |
|---|---|---|
| | 100:1 | 30:1 |
| 2.4 | 62 | 47 |
| 0.8 | 60 | 49 |

Experiment 3

MER was injected IP into BALB/c mice, and their spleens harvested 2, 8, or 15 days later. The splenocytes from the treated mice and from normal controls were then incubated for 6 days with EL4 cells, and their cytotoxic capacity assayed and the results are given in Table 3. Spleen cells taken 2 days after administration of 500 μg MER were virtually without cytotoxic capacity, whereas cells derived on days 8 and 15 after treatment were fully reactive. The smaller amount of MER employed, 100 μg, exerted a potentiating effect on splenocytes harvested on day 2, and was slightly suppressive for splenocytes taken subsequently.

TABLE 3

EFFECT OF TREATMENT OF BALB/c MICE WITH MER ON THE IN VITRO SENSITIZATION OF THEIR SPLENOCYTES AGAINST C57Bl EL4 CELLS

| Amount MER given (IP) to BALB/c Spleen Donors (μg) | Percent Specific $^{51}Cr$ Release from EL4 Cells in Contact with in vitro Sensitized Splenocytes taken from Donors at Following Times after MER treatment at Different Effector/Target Cell Ratios | | | | | |
|---|---|---|---|---|---|---|
| | 2 DAYS | | 8 DAYS | | 15 DAYS | |
| | 30:1 | 10:1 | 30:1 | 10:1 | 30:1 | 10:1 |
| 0 (Control) | 76 | 38 | 72 | 46 | 68 | 42 |
| 100 | 92 | 70 | 62 | 30 | 70 | 27 |
| 500 | 10 | 3 | 75 | 56 | 69 | 40 |

Experiment 4

As is seen from Table 4, "uneducated" splenocytes incubated without MER were devoid of any cytotoxic capacity for the syngeneic target cells. In contrast, exposure of the splenocytes to quantitites of MER ranging from 66 to 0.8 μg effected a definite change to cytotoxic potency, but to a categorically lesser extent than when the splenocytes were exposed to both MER and to the specific EL4 target cells (Table 1). This observation thus suggests a bimodal effect of MER, at least in this system: an influence on the specific education process, i.e. as increased capacity of effector cells to respond to specific antigenic sensitization and an excitation effect which takes place independent of specific antigenic stimulation and which endows certain lympho-reticular cells with a nonspecifically directed ability to cause cell damage.

TABLE 4

EFFECT OF MER IN VITRO ON CYTOTOXIC CAPACITY OF NON-SENSITIZED C57Bl SPLENOCYTES AGAINST C57Bl EL4 LEUKEMIA CELLS

| MER added (μg) to Cultures at Beginning | Percent Specific $^{51}Cr$ Release from EL4 Cells in Contact with Splenocytes at Effector/Target Cell Ratios of | |
|---|---|---|
| | 100:1 | 30:1 |
| 0 (Control) | 3 | 3 |
| 200 | 7 | 6 |

TABLE 4-continued

EFFECT OF MER IN VITRO ON CYTOTOXIC CAPACITY
OF NON-SENSITIZED C57Bl SPLENOCYTES
AGAINST C57Bl EL4 LEUKEMIA CELLS

| MER added (μg) to Cultures at Beginning | Percent Specific $^{51}$Cr Release from EL4 Cells in Contact with Splenocytes at Effector/Target Cell Ratios of | |
|---|---|---|
| | 100:1 | 30:1 |
| 66 | 21 | 20 |
| 22 | 28 | 30 |
| 7.3 | 12 | 11 |
| 2.4 | 21 | 17 |
| 0.8 | 13 | 9 |

Experiments 5 and 6

Further experiments were carried out with two syngeneic mixed lymphoid cell-tumor cell culture (MLTC) systems. In one, splenocytes that were lymph node cells from C57B1/6 mice were sensitized against mitomycin-C inactivated EL-4 leukemia cells (of C57B1/6 origin). In the other, splenocytes from strain A mice were sensitized to YAC leukemia cells (of A origin). Cultures were set up at various responder-stimulator (R/S) cell ratios, in the absence or the presence of varying amounts of MER. The cytotoxic activity of the lymphoid cells against the respective target cells was assessed on day 6 of the MLTC incubation. The results of several representative experiments are presented in Tables 5 and 6.

In these and the subsequent experiments (Experiments 5-9), the "one-way" mixed leukocyte-tumor cell cultures (MLTC) for the generation of cytotoxic effector cells comprise cell mixtures consisting of $5 \times 10^4$–$1 \times 10^6$ mitomycin-C (40–50 μg/$2 \times 10^7$ cells/ml, 30 min. at 37° C.) - treated stimulator (S) leukemia cells and $5 \times 10^6$ lymphoid responder (R) cells prepared in 5 ml enriched RPMI 1640 medium, thus giving responder/stimulator (R/S) cell ratios of 5/1-100/1. The enriched RPMI 1640 culture medium comprises RPMI 1640 (Biolab Laboratories Ltd., Jerusalem, Israel) buffered at pH 7.0 with sodium bicarbonate, and supplemented with 10% heat-inactivated fetal calf-serum (FCS), $5 \times 10^{-5}$M 2-mercaptoethanol, 10 mM Hepes buffer (Sigma Chemical Co., St. Louis, Mo.), 2 mM glutamine, and antibiotics. The leukemic tumors were propagated in ascites form by weekly intraperitoneal passage of $2 \times 10^7$ cells in young, adult syngeneic recipients. These tumors included EL-4, a chemically induced leukemia of C57B1/6 mice, and YAC, a Moloney virus-induced leukemia of strain A mice. Before use, the freshly obtained ascitic tumor cells wer washed 3 times with cold RPMI 1640 medium. The mouse lymphoid cells were prepared as single cell suspensions from the spleens and mesenteric lymph nodes of normal donors, as described in Kedar et al, supra.

As can be seen from Tables 5 and 6, addition of MER to the MLTC cultures at doses ranging from 2.4 to 25 μg per 5 ml cultures (0.5–5 μg/ml) effected an appreciable augmentation (50–200%) of lymphoid cells cytotoxic capacity. This stimulatory effect was more pronounced in splenocyte than in lymph node cultures at suboptimal R/S ratios (10/1–50/1).

Control leukocytes incubated for 6 days without MER and without stimulator leukemia cells were devoid of an apprec cvtotoxic capacitv (less than 5%) for the syngeneic targets. In contrast, exposure of the lymphoid cells to MER only, in quantities ranging from 0.8 to 66 μg per culture, effected a definite change towards cytotoxic potency, although to an appreciably lesser extent, in the majority of the experiments, than when the lymphoid cells were exposed to both MER and stimulator leukemia cells.

In contrast to the stimulatory action of low doses of MER, larger amounts, ranging from 66 to 200 μg per culture, caused a marked suppression (40–90% decrease, as compared with reactivity generated in absence of MER). This effect could not be attributed to any gross toxicity of MER for the lymphoid cells, since the number of trypan blue-excluding cells was similar in cultures exposed or not exposed to 100–200 μg MER. Lymph node cells appeared to be more susceptible to the suppressive effect of large amounts of MER than were splenocytes.

TABLE 5

Effect of addition of MER in vitro on the generation of C57Bl/6 anti-EL-4 leukemia cytotoxic lymphocytes[a]

| Exp. No. | Source of responder cells[b] | Responder/ stimulator ratio in MLTC cultures[c] | Percent specific lysis of $^{51}$Cr—EL-4 targets when following amounts of MER were added to 5 ml effector cell generation cultures | | | | | | |
|---|---|---|---|---|---|---|---|---|---|
| | | | 0 μg | 0.8 μg | 2.4 μg | 7.4 μg | 22 μg | 66 μg | 200 μg |
| 1 | Spleen | 5/1 | 14(0)[d] | 20(4) | 50(15) | 37(10) | 43(28) | 14(7) | 8(3) |
| 2 | Spleen | 10/1 | 24(0) | 22(1) | 35(14) | 50(15) | 60(29) | 44(22) | 12(4) |
| 3 | Spleen | 20/1 | 13(0) | 17(2) | 28(9) | 40(18) | 36(14) | 18(8) | 5(2) |
| 4 | Spleen | 10/1 | 39(2) | 44(5) | 60(13) | 61(15) | 52(18) | 35(13) | 15(3) |
| 5 | Lymph nodes | 5/1 | 20(0) | 20(2) | 27(4) | 40(12) | 35(12) | 10(1) | 2(0) |
| 6 | Lymph nodes | 5/1 | 49(2) | 44(4) | 55(8) | 68(13) | 65(18) | 42(18) | 2(1) |
| 7 | Lymph nodes | 10/1 | 50(0) | 40(3) | 58(5) | 62(4) | 50(2) | 24(2) | 10(1) |
| 8 | Lymph nodes | 20/1 | 39(0) | 45(1) | 57(3) | 56(10) | 46(3) | 42(1) | 10(0) |

[a] A total of 14 experiments were performed; similar patterns of reactivity were seen in 11 of the 14 experiments, whereas in the other 3 experiments no significant increase in cytotoxicity was observered using small amounts of MER.
[b] For each individual experiment, cell preparations were pooled from 4–5 mice.
[c] For each experimental group, MLTC cultures were set up in triplicate using 17 × 100 tissue culture tubes with a total volume of 5 ml. Each culture consisted of 5 × 10$^6$ responder cells and varying numbers of mitomycin C-treated stimulator leukemia cells. After 6 days, the cells from replicate cultures were pooled, washed once, and tested for cytotoxic capacity.
[d] The values represent the means of triplicate determinations for each MLTC pool (after subtracting the amount of $^{51}$Cr released by target cells incubated in medium alone) using an effector/target cells ratio of 30/1. The values in parentheses represent the means of triplicate determinations of cultures where equal numbers of lymphoid cells were incubated without leukemia stimulator cells. Similar pattern of reactivity was seen using an effector/target ratio of 10/1.

The data of Tables 5, 6 and 7 suggest that the stimulatory effect on splenocytes of small amounts of MER, in the majority of the experiments, cannot be ascribed only to an addition of the non-specific effect to the usual specific sensitization process. It is more likely that the increase in cytotoxicity represents not only the non-specific stimulation but also the addition of the synergistic potentiation of specific sensitization. This is exemplified in Table 5, experiment No. 1, where C571/6 splenocytes sensitized to EL-4 show 14% target cell lysis, splenocytes cultured with 2.4 μg MER alone give 15% lysis, and splenocytes sensitized to EL-4 in the presence of MER give 50% lysis.

TABLE 6

Effect of addition of MER in vitro on the generation of A anti-YAC leukemia cytotoxic lymphocytes[a]

| Exp. No. | Responder/ stimulator ratio in MLTC cultures[b] | Percent specific lysis of $^{51}$Cr—YAC targets when following amounts of MER were added to 5 ml effector cell generation cultures. | | | | | | |
|---|---|---|---|---|---|---|---|---|
| | | 0 μg | 6 μg | 12 μg | 25 μg | 50 μg | 100 μg | 200 μg |
| 1 | 2.5/1 | 5(1) | 3 | ND | 31(6) | 7(6) | ND | 5(1) |
|   | 10/1 | 2(0) | 8 | ND | 6 | 8 | ND | 5(1) |
| 2 | 5/1 | 11(3) | 22(6) | 23(7) | 21(8) | 13(10) | 13(4) | 4(2) |
|   | 10/1 | 10(0) | 9(2) | 25(7) | 17(5) | 15(8) | 10(3) | 8(2) |

[a]5 experiments were performed; similar patterns of reactivity were seen in 4 of these experiments. No significant increase in cytotoxicity was observed in the other experiment.
[b]Cultures consisted of spleen cells from strain A mice and mitomycin C-inactivated YAC leukemia stimulator cells.
For additional details, see legends c and d to Table 5.
ND = not done

Experiment 7

Table 7 depicts the results of several representative experiments carried out with BALB/c splenocytes and lymph node cells sensitized to EL-4 leukemia cells. With the spleen cells, the results were similar to those obtained with syngeneic responder cells, although the stimulatory action of MER in the allogeneic system, with its high reactivity even in the absence of the agent, was less pronounced. With lymph node cultures, no appreciable increase in effector cytotoxicity was produced by low doses of MER, but strong suppression was elicited by the higher amounts.

leukemia cells was also found in human lymphoid cell cultures exposed to MER alone (Table 9). Under the culture conditions employed, fetal calf serum (but not human AB serum) was able by itself to incite an appreciable cytotoxicity, as was already known. Addition of MER to the human lymphocyte cultures, containing either FCS or AB serum, provoked strong cytotoxic reactivity towards EL-4 cells, to a much greater extent than was produced by the FCS alone In contrast to the nonspecific cytotoxic activity induced by MER, specific sensitization with the same leukemic cells used in the present work leads to specific cytotoxic capacity for the sensitizing cells.

TABLE 8

Nonspecific induction of cytotoxic activity in mouse spleen cell cultures by MER[a]

Percent specific lysis of $^{51}$Cr—target cells:[b]

TABLE 7

Effect of addition of MER in vitro on the generation of BALB/c anti-EL-4 cytotoxic lymphocytes[a]

| Exp. No. | Source of responder cells | Responder/ stimulator ratio | Percent specific lysis of $^{51}$Cr—EL-4 targets when following amounts of MER were added to 5 ml effector cell generation cultures[b] | | | | | | |
|---|---|---|---|---|---|---|---|---|---|
| | | | 0 | 0.8 μg | 2.4 μg | 7.4 μg | 22 μg | 66 μg | 200 μg |
| 1 | Spleen | 20:1 | 79(0) | 83(3) | 88(3) | 93(3) | 91(6) | 80(2) | 55(2) |
| 2 | Spleen | 30:1 | 90(0) | 93(2) | 93(2) | 100(4) | 98(4) | 80(3) | 48(1) |
| 3 | Spleen | 50:1 | 75(0) | 80(3) | 92(6) | 97(8) | 95(6) | 70(4) | 22(0) |
| 4 | Spleen | 100:1 | 64(0) | 73(2) | 80(8) | 84(10) | 83(7) | 60(4) | 28(1) |
| 5 | Lymph nodes | 10:1 | 68(0) | 70(1) | 72(2) | 75(1) | 47(1) | 32(1) | 6(1) |
| 6 | Lymph nodes | 20:1 | 56(0) | 55(0) | 62(1) | ND | 45(0) | ND | 5(0) |
| 7 | Lymph nodes | 30:1 | 80 | 78 | 79 | 70 | 69 | 55 | 2 |

[a]12 experiments were performed; similar pattern of reactivity was noted in 10 of the 12 experiments. No significant increase in cytotoxicity was observed in the other 2 experiments.
[b]Cytotoxic activity was measured at an effector/target cell ratio of 10/1
ND = not done
For additional general details, see legends c and d to Table 5.

Experiment 8

The initial experiments demonstrated the ability of MER to render mouse splenocytes cytotoxic for murine leukemia cells even without a specific sensitizing exposure. This phenomenon has now been investigated further, employing additional cell combinations of both mouse and human origin. In these experiments, splenocytes derived from normal BALB/c, C57Bl/6 and A mice, and Ficoll-Hypaque enriched human peripheral blood lymphocytes (80–85% pure), were cultured with various quantitites of MER for 6 days without any stimulating cells. At the end of the incubation period, cell-mediated cytotoxicity (CMC) was assayed against EL-4 and YAC leukemia cells.

The results shown in Table 8 indicate that significant cytotoxic activity developed in all the mouse cell combinations tested, most clearly in the presence of 20 μg MER. Nonspecific induction of cytotoxicity for EL-4

| Spleen cells (Haplotype) | EL-4 (H-2[b]) | | | | YAC (H-2[a]) | | | |
|---|---|---|---|---|---|---|---|---|
| | μg MER added to effector cell generation cultures | | | | | | | |
| | 0 | 2 | 20 | 200 | 0 | 2 | 20 | 200 |
| BALB/c (H-2[d]) | 2 | 9 | 17 | 4 | 1 | 3 | 17 | 6 |
| C57Bl (H-2[b]) | 2 | 12 | 21 | 13 | 0 | 4 | 12 | 4 |
| A (H-2[a]) | | ND | | | 1 | 7 | 9 | 3 |

[a]Spleen cells (5 × 10[6], in 5 ml) from normal mice were cultured for 6 days with the various amounts of MER.
[b]Values represent the means of triplicate determinations on each splenocyte pool of one experiment using an effector/target cell ratio of 30/1. Similar results were seen in 5 additional experiments.
ND = not done

TABLE 9

Nonspecific induction of cytotoxic activity in human lymphoid cell cultures by MER[a]

| Exp. No. | Blood Donor (Name) | Type of serum in culture medium | Percent specific lysis of $^{51}$Cr—EL-4 target cells[b] μg MER added to effector cell generation cultures | | | | |
|---|---|---|---|---|---|---|---|
| | | | 0 | 3 | 10 | 30 | 100 |
| 1 | C. O. | FCS | 24 | 37 | 48 | 44 | 40 |
|   | B. A. | FCS | 22 | 53 | 67 | 55 | 49 |
| 2 | D. C. | FCS | 15 | 36 | 53 | 37 | 30 |
|   |       | AB  | 0  | 18 | 44 | 37 | 24 |
| 3 | M. K. | FCS | 25 | ND | 69 | 64 | ND |
|   |       | AB  | 0  | ND | 58 | 36 | ND |

[a]Ficoll-Hypaque separated human peripheral blood lymphoid cells (2.5 × 10$^6$, in 3 ml) were cultured for 6 days with the specified amount of MER in RPMI 1640 medium containing 10% fetal calf serum (FCS) or heterologous human AB serum.
[b]Values represent the means of triplicate determinations for each lymphocyte preparation, using an effector/target cell ratio of 10/1.
ND = not done

Experiment 9

Efforts to characterize the cells which are stimulated by MER were carried out by using the nylon-wool column fractionation technique. Spleen cells from BALB/c and C571/6 mice were fractionated either before or after sensitization to EL-4 leukemia cells (carried out for 6 days, with or without 2 μg/ml of MER in the culture). To ascertain the development of any nonspecific induced cytotoxicity, cultures consisting of whole and of non-adherent splenocyte populations (with or without MER) in the absence of stimulator leukemia cells were included in all the experiments.

Nylon column separation of unsensitized spleen cells was carried out under sterile conditions. Columns were prepared with 700 mg of nylon wool fibers (Leukopak, Fenwal Laboratories, Div. Travenol Laboratories, Morton Grove, Ill.) using the barrel of a 5 ml plastic syringe. Before use, the column was autoclaved, washed with 10% FCS - RPMI 1640 and prewarmed to 37° C. Spleen cells suspended in 10% FCS - RPMI 1640 (150×10$^6$, 2 ml, at 37° C.) were introduced into the column, which was then incubated at 37° C. for 45 min. The non-adhering cells were then recovered by washing the column with 15 ml of warmed medium. Sensitized cells obtained from MLTC (10×10$^6$, in 0.5 ml) were filtered over small nylon columns made in Pasteur pipettes, by the same procedure. The eluted cells were spun down and resuspended in fresh medium to the desired concentration. Viable cell recovery was 30-40% of the cell input in both cases.

The results of a representative experiment are shown in Table 10. Removal of nylon-adherent cells from the responder cell population either before or after sensitization did not impair the potentiating activity of MER on specific sensitization, nor did it dimish the nonspecific induction of cytotoxicity. In fact, the elevation in cytotoxicity effected by MER was even more pronounced after removal of the nylon-adherent cells. These findings suggest that MER exerts its stimulatory effects (both specific and nonspecific) on splenocytes by activating the non-adherent, lymphoid population of the spleen.

TABLE 10

Effect of addition of MER in vitro on the generation of cytotoxic lymphocytes by unfractionated and nylon-wool column-fractionated spleen cells[a]

| Treatment of spleen cells | Presence of MER (2 μg/ml) in culture | Presence of stimulator EL-4 cells in culture | Percent specific lysis of $^{51}$Cr—EL-4 targets effected by splenocytes from:[b] | |
|---|---|---|---|---|
| | | | BALB/c donors | C57Bl/6 donors |
| Unfractionated | − | − | 0 | 0 |
| | − | + | 73 | 19 |
| | + | − | 5 | 8 |
| | + | + | 85 | 34 |
| Fractionated before sensitization[c] | − | − | 0 | 0 |
| | − | + | 82 | 24 |
| | + | − | 12 | 16 |
| | + | + | 99 | 49 |
| Fractionated after sensitization[c] | − | − | 0 | 0 |
| | − | + | 88 | 36 |
| | + | − | 8 | 12 |
| | + | + | 99 | 46 |

[a]Five million spleen cells were cultured for 6 days with or without EL-4 cells, employing a R/S ratio of 20:1 with BALB/c cells and of 5:1 with C57Bl/6 cells.
[b]Values represent the means of triplicate determinations for each splenocyte pool in one experiment. Similar results were obtained in 2 additional experiments.
[c]Only the non-adhering cells were tested.

The observations described in the above experiments open the way for a new means of immuno-therapy of human cancer patients to be referred to as "passive or adoptive cancer immunotherapy by means of MER-stimulated effector cells" or briefly as "passive MER therapy". The following exeriments 10 through 14 employing mouse-leukemia models show that in vitro stimulated effector cells do indeed possess marked antitumor efficacy when injected into tumor-bearing mice and it is expected that this is especially so when the tumor-bearing recipient is also treated actively with MER in conjunction with the passive-adoptive immunotherapy by means of MER-stimulated effector cells. Thus, in human patients as well, while the passive MER therapy may be given alone, it is preferably given in conjunction with other treatment modalities, including direct administration to the patient of MER or other non-specific immunostimulators.

Experiments 10-14

The following Tables 11-15 indicate the results of laboratory tests employing mouse leukemia models. Table 11 shows a very marked anti-tumor efficacy of both syngeneic and allogeneic sensitized lymphocytes. The survival rate after 90 days is extremely small when the mice are injected with the leukemia cells alone or in addition to unsensitized lymphocytes. However, when the mice are treated with the leukemia cells as well as the sensitized lymphocytes, be they syngeneic or allogeneic, outstanding survival rates appear. It is apparent, however, that the lymphocytes must be sensitized to the particular leukemia.

Table 12 shows the results of a similar experiment using strain A mice and YAC leukemia. Again, the sensitized lymphocytes provide a very marked antitumor efficacy.

Table 13 shows that the mice treated with the sensitized lymphocytes can even withstand a second challenge with leukemia cells.

Tabl 14 shows the effectiveness of combined chemoimmunotherapy as well as treatment with the sensitized lymphocytes. It can be seen that the passive immunotherapy substantially improves the effects of the chemotherapeutic agent used in the test.

Table 15 is similar to Table 14 but deals with YAC leukemia in A strain mice.

TABLE 11
PREVENTION OF EL4 LEUKEMIA IN C57BL/6 MICE BY SYNGENEIC AND ALLOGENEIC SPLENOCYTES SENSITIZED IN VITRO*

| CELL MIXTURE | No. SURVIVORS/TOTAL by day 90 | |
|---|---|---|
| EL4 alone | 2/69 | (3%) |
| EL4 + Normal C57BL/6 Lymphocytes | 2/24 | (8%) |
| EL4 + Sensitized C57BL/6 Lymphocytes | 28/30 | (93%) |
| EL4 + Normal BALB/C Lymphocytes | 2/44 | (5%) |
| EL4 + Sensitized BALB/C Lymphocytes | 49/57 | (86%) |
| EL4 + BALB/C Lymphocytes sensitized to YAC leukemia | 0/8 | (0%) |

*$2 \times 10^4$ leukemia cells and $2-4 \times 10^6$ lymphocytes inoculated SC.

TABLE 12
PREVENTION OF YAC LEUKEMIA IN STRAIN A MICE BY BALB/C SPLENOCYTES SENSITIZED IN VITRO

| SENSITIZATION CELL MIXTURE | No. SURVIVORS/ TOTAL by day 90 | SURVIVAL TIME (range) |
|---|---|---|
| YAC alone | 1/29 | 21-35 |
| YAC + Normal BALB/C lymp. | 1/35 | 19-28 |
| YAC + Sensitized BALB/C lymp. | 35/42 | 31-72 |
| YAC + BALB/C Sensitized to EL4 leukemia | 0/8 | 18-23 |

$2 \times 10^4$ leukemia cell and $2-4 \times 10^6$ lymphocytes inoculated SC.

TABLE 13
RESISTANCE OF C57BL/6 MICE SURVIVING WINN ASSAY TO SECOND CHALLENGE WITH EL4 LEUKEMIA

| GROUP | No. SURVIVORS/TOTAL by day 90 | RANGE OF SURVIVAL TIME (days) |
|---|---|---|
| CONTROL MICE | 0/25 | 12-18 |
| TREATED MICE* | 26/35 | 29-60 |

*MICE SURVIVING WINN ASSAYS WERE INOCULATED I.P. ON DAYS 75-90 WITH $1 \times 10^6$ EL4 CELLS.

TABLE 14
CHEMOIMMUNOTHERAPY OF EL4 LEUKEMIA IN C57BL/6 MICE WITH SYNGENEIC EFFECTOR CELLS

| TREATMENT | % SURVIVORS (day 80) |
|---|---|
| EL4 ($1 \times 10^3$, DAY 0) | 0 |
| EL4 + CY* (2 mg, day + 1) | 33 |
| EL4 + CY + Normal Lymphocytes ($10 \times 10^6$, day + 2) | 40 |
| EL4 + CY + Immune Lymphocytes ($10 \times 10^6$, day + 2) | 100 |

*Cytoxan (cyclophosphamide)

TABLE 15
CHEMOIMMUNOTHERAPY OF YAC LEUKEMIA IN A MICE WITH ALLOGENEIC EFFECTOR CELLS

| TREATMENT | PERCENT SURVIVORS 90 days |
|---|---|
| YAC alone | 0 (30 days) |
| YAC + Cytoxan | 60 |
| YAC + Normal Lymphocytes | 0 |
| YAC + Immune Lymphocytes | 10 |
| YAC + Cytoxan + Normal Lymphocytes | 60 |
| YAC + Cytoxan + Immune Lymphocytes | 100 |

YAC: $1 \times 10^3$ I.P. or $2 \times 10^4$ S.C., day 0
Cytoxan: 4 mg IP, day + 1
Lymphocytes: BALB/C, $10 \times 10^6$, IP, day + 2

The clinical procedures for passive MER Therapy in humans will be as follows:

a. White blood cells (WBC) in large numbers are obtained from patients by the established techniques, employing cell-separator technology.

b. The WBC are to be obtained preferably from patients in a state of remission (leukemia) or relative quiescence of disease (solid neoplasms), as brought about by conventional means of therapy. In the case of solid cancers where there is no invasion of cancer cells into the blood stream, WBC can also be obtained from patients in active disease, once it is confirmed that the blood is indeed free of any living tumor cells.

c. The WBC are stimulated in vitro to become cytotoxic to the patent's tumor cells. Several possible means to accomplish this stimulation present themselves:

(i) Incubation of the WBC with MER and the patient's own tumor cells, obtained previously from his blood (in cases of leukemia), from biopsy material (solid tumors), or from tumor tissue removed at surgery (also, solid tumors).

(ii) Incubation of the WBC with MER and tumor cells of the same type obtained from another patient with similar malignant disease.

(iii) Incubation of the WBC with MER and tumor cells of lines maintained in the laboratory which originate from a tumor of similar type. It is noted that tumor cells of the same histological type are known, in at least some instances, to express common tumor-associated cell-surface antigens, thus making possible specific sensitization of the lymphoid tissue cells from one patient against his own tumor cells by means of exposure to allogeneic tumor cells of the same type.

(iv) Incubation of the WBC with MER only.

d. After in vitro stimulation and removal of all traces of MER by means of gradient centrifugation, the WBC are cryopreserved until use. It is noted that the remaining of traces of MER with the cells does not represent a problem, as human cancer patients have been treated by administration intravenously of very much larger amounts of MER, with no major undesirable side-effects reported.

e. As needed, the stimulated WBC will be thawed and injected intravenously to the patient. This may be with the patient's own WBC (=autochthonous, adoptive treatment), or with WBC from pools of such cells obtained from normal human donors (or from blood bank pools) and stimulated in vitro with MER with or without tumor cells of a given type, as indicated above (=allogeneic, passive treatment).

f. Work now in progress may identify the subpopulations of lymphocytes and/or monocytes (macrophagic cells) in the WBC which are stimulated to cytotoxic anti-tumor cell reactivity in vitro. In that event, the cells to be injected to the patient upon need may be the relevant subpopulations.

g. A variation on the procedur indicated under e and f above is to freeeze the WBC or relevant subpopulations before in vitro stimulation, and to effect in vitro stimulation to cytotoxic capacity after thawing and immediately before injection to the patient.

h. The injection of allogeneic WBC or WBC subpopulations and even the injection of such cells of autochthonous origin after in vitro stimulation, could conceivably lead to the development of disease of the graft-versus-host (GvH) type, especially in patients whose immunological capacity is depressed as a consequence of their disease and of conventional treatment. Accordingly, effort will be made to selectively remove any clones of effector cells reactive against the patient's own normal tissues, by the absorption procedures already worked out in mouse cell models. Bonavida et al, "Transplantation of allogeneic lymphoid cells specifically depleted of graft versus host reactive cells", Nature 249, 658–659 (1974).

i. Injection of the effector cells will be initiated upon indication of disease relapse or progression. The numbers of effector cells to be injected and the schedule of this treatment must be determined empirically. The obvious purpose of such passive or adoptive therapy with MER-stimulated effector cells is the attack by these cells on the cancer cells in the host. Such treatment can also be profitably employed even in patients which do not show disease relapse or progression, and in patients following surgery or other intensive conventional treatment who appear to be tumor-free thereafter, but in whom residual microscopic foci of neoplastic tissue pose a threat of renewed disease in the future.

It should be understood that the content of the culture media and the culturing conditions used during the sensitization step of the present inveltion, whether or not stimulator cells are present, should be optimized in the manner known in the art from the Kedar et al publication incorporated by reference hereinabove. The present invention does not relate per se to the conditions required for sensitization but to the discovery that the cytotoxic reactivity may be greatly potentiated by the presence of MER and that non-specific cytotoxicity may be imparted to the receptor cells by the presence of MER even in the absence of stimulator cells. Accordingly, the terminology "conditions at which cytotoxic reactivity is imparted to the lymphocytes" refers to the art-recognized conditions of culture medium content, R/S ratio and other culture parameters as set forth in the Kedar et al publication and as exemplified in the experiments set forth in the specification.

Furthermore, while preferred amounts are set forth in the present specification for the amount of MER which should be present in the culture and the ratio of lymphocytes to cancer cells (R/S ratio), those skilled in the art will understand from a reading of the present specification that the optimum cytotoxicity potentiating amount of MER and R/S ratio can be determined by routine experimentation for any given type of receptor cell (including human lymphoid tissue) or other culture conditions. For example, the R/S ratio for human lymphocytes has been found to be optimum at about 4/1.

It will be obvious to those skilled in the art that various changes may be made without departing from the scope of the invention and the invention is not to be considered limited to what is described in the specification.

What is claimed is:

1. In the method of stimulating lymphocytes to specific cytotoxic reactivity against cancer cells comprising incubating in vitro the lymphocytes in contact with the corresponding cancer cells under conditions at which specific cytotoxic reactivity is imparted to the lymphocytes, the improvement, whereby the specific cytotoxic reactivity is greatly potentiated, comprising: adding to the culture of lymphocytes and cancer cells a cytotoxic reactivity potentiating amount of MER.

2. A method in accordance with claim 1, wherein said MER is added to the culture within the first 48 hours of culture.

3. A method in accordance with claim 1, wherein said MER is added to the culture within the first 24 hours of culture.

4. A method in accordance with claim 1, wherein about 0.2–5 µg/ml MER is added to the culture.

5. A method in accordance with claim 1, wherein the culture contains a ratio of lymphocyte cells to cancer cells of 4/1 to 100/1.

* * * * *